US011846640B2

(12) United States Patent
Ferrandez et al.

(10) Patent No.: US 11,846,640 B2
(45) Date of Patent: Dec. 19, 2023

(54) IDENTIFICATION OF ANTICOAGULANTS IN A SAMPLE

(71) Applicant: DSM IP Assets B.V., Heerlen (NL)

(72) Inventors: Abel Ferrandez, Kaiseraugst (CH); Anne Brisset, Kaiseraugst (CH)

(73) Assignee: PENTAPHARM AG, Aesch Bl (CH)

( * ) Notice: Subject to any disclaimer, the term of this patent is extended or adjusted under 35 U.S.C. 154(b) by 0 days.

(21) Appl. No.: 16/378,729

(22) Filed: Apr. 9, 2019

(65) Prior Publication Data
US 2019/0302132 A1    Oct. 3, 2019

Related U.S. Application Data

(63) Continuation of application No. 15/102,944, filed as application No. PCT/EP2014/077084 on Dec. 9, 2014, now abandoned.

(30) Foreign Application Priority Data

Dec. 9, 2013 (CH) ...................................... 2038/13

(51) Int. Cl.
*G01N 33/86* (2006.01)

(52) U.S. Cl.
CPC ....... *G01N 33/86* (2013.01); *G01N 2333/745* (2013.01); *G01N 2333/96433* (2013.01); *G01N 2333/96444* (2013.01); *G01N 2333/974* (2013.01)

(58) Field of Classification Search
CPC ......... G01N 33/86; G01N 2333/96433; G01N 2333/745; G01N 2333/96444; G01N 2333/974
See application file for complete search history.

(56) References Cited

U.S. PATENT DOCUMENTS

2015/0185235 A1* 7/2015 Sommer ................ G01N 33/86
                                                                 702/19

OTHER PUBLICATIONS

Perkins et al., Thrombosis Diathesis Haemorrhagica, 1964, 11: 254-266. (Year: 1964).*
Nash et al. (Analytical Biochemistry, 1984, 138: 319-323, abstract is attached. (Year: 1984).*
International Search Report for PCT/EP2014/077084, 4 pages, dated Mar. 18, 2015.
Harder et al., "Monitoring direct FXa-inhibitors and fondaparinux by Prothrombinase-induced Clotting Time (PiCT): Relation to FXa-activity and influence of assay modifications", Thrombosis Research, vol. 123, No. 2, 1, pp. 396-403 (Dec. 2008).
Graff et al., "Effects of the Oral, Direct Factor Xa Inhibitor Rivaroxaban on Platelet-Induced Thrombin Generation and Prothrombinase Activity", Journal of Clinical Pharmacology, vol. 47, No. 11, pp. 1398-1407 (2007).
Graff et al., "Monitoring effects of direct FXa-inhibitors with a new one-step prothrombinase-induced clotting time (PiCT) assay: comparative in vitro investigation with heparin, enoxaparin fondaparinux and DX 9065a", International Journal of Clinical Pharmacology and Therapeutics vol. 45, No. 4, pp. 237-243 (Apr. 1, 2007).
Clemens et al., "Switching from enoxaparin to dabigatran etexilate: pharmacokinetics, pharmacodynamics, and safety profile", European Journal of Clinical Pharmacology vol. 68, No. 5, pp. 607-616 (Jan. 18, 2012).
Kluft et al., "Preincubation in the Prothrombinase-induced Clotting Time test (PiCT) is necessary for in vitro evaluation of fondaparinux and to be avoided for the reversible, direct factor Xa inhibitor, rivaroxaban", International Journal of Laboratory Hematology, vol. 35, No. 4, pp. 379-384 (Nov. 14, 2012).
Salmela et al., "Comparison of monitoring methods for lepirudin: Impact of warfarin and lupus anticoagulant", Thrombosis Research, vol. 125, No. 6, pp. 538-544 (Jun. 1, 2010).
Kuczka et al., "Biomarkers and Coagulation Tests for Assessing the Biosimilarity of a Generic Low-Molecular-Weight Heparin: Results of a Study in Healthy Subjects with Enoxaparina", The Journal of Clinical Pharmacology, vol. 48, No. 10, pp. 1189-1196 (Oct. 1, 2008).
Samama et al., "Laboratory assessment of new anticoagulants", Product Information Clinical Chemistry and Oaboratory Medicine (CCLM), vol. 49, No. 5, pp. 761-772 (Feb. 3, 2011).
Akimoto et al., "Anticoagulation with Argatroban for Elective Percutaneous Coronary Intervention: Population Pharmacokinetics and Pharmacokinetic-Pharmacodynamic Relationship of Coagulation Parameters", Journal of Clinical Pharmacology, vol. 51, No. 6, pp. 805-818 (Jun. 1, 2011).
Samama et al., "Assessment of laboratory assays to measure rivaroxaban—an oral, direct factor Xa inhibitor", Thrombosis and Haemostasis, vol. 103, No. 4, pp. 815-825 (Apr. 1, 2010).
Pefakit PICT, Product Manual and Manufacturer Pentapharm (2009).

* cited by examiner

*Primary Examiner* — Allison M Fox
*Assistant Examiner* — Qing Xu
(74) *Attorney, Agent, or Firm* — Nixon & Vanderhye, PC

(57) ABSTRACT

The present invention is directed to a novel method of determining inhibitors of proteolytically active coagulation factors, referred to herein as anticoagulants, in a sample, in particular the qualitative detection of direct thrombin and factor Xa inhibitors in a sample. The method of the present invention allows a qualitative determination of the nature anticoagulants present in a sample. This can be achieved with only one coagulation-based test. The method can be used in a test kit, including a point-of-care (POC) system.

17 Claims, 10 Drawing Sheets

Figure 2.

|  |  | A | B | C | D | E | F |
|---|---|---|---|---|---|---|---|
| NPP | 0.0 | 24.6 | 52.8 | 29.3 | 10.8 | 26.2 | 82.9 |
| UFH (IU/mL) | 0.3 | 60.2 | 220.1 | 54.8 | 10.9 | 28.4 | 80.6 |
|  | 0.6 | 93.3 | 300.0 | 119.5 | 11.4 | 27.2 | 76.1 |
|  | 0.8 | 106.5 | 300.0 | 186.7 | 11.5 | 26.5 | 68.4 |
|  | 1.2 | 127.7 | 300.0 | 300.0 | 12.5 | 26.4 | 60.0 |
| LMWH (IU/mL) | 0.4 | 69.1 | 300.0 | 44.0 | 11.0 | 27.4 | 81.4 |
|  | 0.7 | 95.2 | 300.0 | 61.4 | 11.6 | 31.8 | 142.7 |
|  | 1.0 | 114.7 | 300.0 | 81.3 | 11.5 | 26.1 | 43.5 |
|  | 1.5 | 139.4 | 300.0 | 125.5 | 12.1 | 26.5 | 47.0 |
| Fonda (µg/mL) | 0.3 | 53.8 | 123.3 | 31.8 | 11.1 | 31.1 | 80.6 |
|  | 1.0 | 75.0 | 290.1 | 33.4 | 11.5 | 46.8 | 84.7 |
|  | 1.3 | 78.7 | 300.0 | 34.1 | 11.6 | 49.5 | 94.7 |
|  | 1.8 | 83.5 | 300.0 | 34.6 | 11.9 | 58.2 | 89.6 |
| Hirudin (µg/mL) | 0.4 | 59.3 | 300.0 | 54.9 | 12.0 | 65.6 | 300.0 |
|  | 1.5 | 139.9 | 300.0 | 75.9 | 13.8 | 165.0 | 300.0 |
|  | 2.5 | 210.9 | 300.0 | 84.9 | 15.0 | 270.0 | 300.0 |
|  | 3.0 | 241.4 | 300.0 | 88.5 | 15.6 | 300.0 | 300.0 |
| Argatroban (µg/mL) | 0.3 | 79.8 | 174.9 | 50.7 | 13.9 | 70.7 | 300.0 |
|  | 1.0 | 108.3 | 287.5 | 70.3 | 22.0 | 95.5 | 300.0 |
|  | 1.5 | 118.4 | 300.0 | 79.0 | 28.1 | 105.2 | 300.0 |
|  | 2.0 | 126.4 | 300.0 | 85.8 | 32.8 | 113.1 | 300.0 |
| Dabi (ng/mL) | 50 | 45.3 | 149.3 | 41.9 | 11.6 | 47.6 | 184.8 |
|  | 150 | 72.3 | 244.5 | 54.7 | 13.0 | 76.0 | 300.0 |
|  | 300 | 95.1 | 300.0 | 68.3 | 14.9 | 88.9 | 300.0 |
|  | 600 | 105.6 | 300.0 | 84.7 | 20.2 | 100.0 | 300.0 |
| Riva (ng/mL) | 50 | 19.2 | 120.3 | 33.9 | 12.3 | 26.9 | 188.9 |
|  | 150 | 23.9 | 169.0 | 38.6 | 16.1 | 35.5 | 284.3 |
|  | 300 | 28.6 | 210.2 | 45.0 | 20.6 | 44.4 | 300.0 |
|  | 600 | 36.3 | 277.0 | 55.4 | 31.2 | 55.4 | 300.0 |
| Apixa (ng/mL) | 50 | 20.0 | 210.2 | 31.1 | 11.5 | 26.4 | 148.4 |
|  | 150 | 23.6 | 141.4 | 33.2 | 12.7 | 33.0 | 236.2 |
|  | 300 | 26.7 | 174.4 | 34.7 | 14.8 | 38.2 | 300.0 |
|  | 600 | 31.3 | 225.6 | 38.7 | 19.3 | 46.6 | 300.0 |

Figure 3.

|  |  | A | B | C | D | E | F |
|---|---|---|---|---|---|---|---|
| NPP | 0.0 | 24.6 | 52.8 | 29.3 | 10.8 | 26.2 | 82.9 |
| UFH (IU/mL) | 0.3 | 60.2 | 220.1 | 54.8 | 10.9 | 28.4 | 80.6 |
|  | 0.6 | 93.3 | 300.0 | 119.5 | 11.4 | 27.2 | 76.1 |
|  | 0.8 | 106.5 | 300.0 | 186.7 | 11.5 | 26.5 | 68.4 |
|  | 1.2 | 127.7 | 300.0 | 300.0 | 12.5 | 26.4 | 60.0 |
| LMWH (IU/mL) | 0.4 | 69.1 | 300.0 | 44.0 | 11.0 | 27.4 | 81.4 |
|  | 0.7 | 95.2 | 300.0 | 61.4 | 11.6 | 31.8 | 142.7 |
|  | 1.0 | 114.7 | 300.0 | 81.3 | 11.5 | 26.1 | 43.5 |
|  | 1.5 | 139.4 | 300.0 | 125.5 | 12.1 | 26.5 | 47.0 |
| Hirudin (µg/mL) | 0.4 | 59.3 | 300.0 | 54.9 | 12.0 | 65.6 | 300.0 |
|  | 1.5 | 139.9 | 300.0 | 75.9 | 13.8 | 165.0 | 300.0 |
|  | 2.5 | 210.9 | 300.0 | 84.9 | 15.0 | 270.0 | 300.0 |
|  | 3.0 | 241.4 | 300.0 | 88.5 | 15.6 | 300.0 | 300.0 |
| Argatroban (µg/mL) | 0.3 | 79.8 | 174.9 | 50.7 | 13.9 | 70.7 | 300.0 |
|  | 1.0 | 108.3 | 287.5 | 70.3 | 22.0 | 95.5 | 300.0 |
|  | 1.5 | 118.4 | 300.0 | 79.0 | 28.1 | 105.2 | 300.0 |
|  | 2.0 | 126.4 | 300.0 | 85.8 | 32.8 | 113.1 | 300.0 |
| Dabi (ng/mL) | 50 | 45.3 | 149.3 | 41.9 | 11.6 | 47.6 | 184.8 |
|  | 150 | 72.3 | 244.5 | 54.7 | 13.0 | 76.0 | 300.0 |
|  | 300 | 95.1 | 300.0 | 68.3 | 14.9 | 88.9 | 300.0 |
|  | 600 | 105.6 | 300.0 | 84.7 | 20.2 | 100.0 | 300.0 |
| Riva (ng/mL) | 50 | 19.2 | 120.3 | 33.9 | 12.3 | 26.9 | 188.9 |
|  | 150 | 23.9 | 169.0 | 38.6 | 16.1 | 35.5 | 284.3 |
|  | 300 | 28.6 | 210.2 | 45.0 | 20.6 | 44.4 | 300.0 |
|  | 600 | 36.3 | 277.0 | 55.4 | 31.2 | 55.4 | 300.0 |
| Apixa (ng/mL) | 50 | 20.0 | 101.4 | 31.1 | 11.5 | 26.4 | 148.4 |
|  | 150 | 23.6 | 141.4 | 33.2 | 12.7 | 33.0 | 236.2 |
|  | 300 | 26.7 | 174.4 | 34.7 | 14.8 | 38.2 | 300.0 |
|  | 600 | 31.3 | 225.6 | 38.7 | 19.3 | 46.6 | 300.0 |

Figure 4.

|  |  | A | B | C | D | E | F |
|---|---|---|---|---|---|---|---|
| NPP |  | 0.0 | 24.6 | 52.8 | 29.3 | 10.8 | 26.2 | 82.9 |
| UFH (IU/mL) | 0.3 | 60.2 | 220.1 | 54.8 | 10.9 | 28.4 | 80.6 |
|  | 0.6 | 93.3 | 300.0 | 119.5 | 11.4 | 27.2 | 76.1 |
|  | 0.8 | 106.5 | 300.0 | 186.7 | 11.5 | 26.5 | 68.4 |
|  | 1.2 | 127.7 | 300.0 | 300.0 | 12.5 | 26.4 | 60.0 |
| LMWH (IU/mL) | 0.4 | 69.1 | 300.0 | 44.0 | 11.0 | 27.4 | 81.4 |
|  | 0.7 | 95.2 | 300.0 | 61.4 | 11.6 | 31.8 | 142.7 |
|  | 1.0 | 114.7 | 300.0 | 81.3 | 11.5 | 26.1 | 43.5 |
|  | 1.5 | 139.4 | 300.0 | 125.5 | 12.1 | 26.5 | 47.0 |
| Hirudin (µg/mL) | 0.4 | 59.3 | 300.0 | 54.9 | 12.0 | 65.6 | 300.0 |
|  | 1.5 | 139.9 | 300.0 | 75.9 | 13.8 | 165.0 | 300.0 |
|  | 2.5 | 210.9 | 300.0 | 84.9 | 15.0 | 270.0 | 300.0 |
|  | 3.0 | 241.4 | 300.0 | 88.5 | 15.6 | 300.0 | 300.0 |
| Argatroban (µg/mL) | 0.3 | 79.8 | 174.9 | 50.7 | 13.9 | 70.7 | 300.0 |
|  | 1.0 | 108.3 | 287.5 | 70.3 | 22.0 | 95.5 | 300.0 |
|  | 1.5 | 118.4 | 300.0 | 79.0 | 28.1 | 105.2 | 300.0 |
|  | 2.0 | 126.4 | 300.0 | 85.8 | 32.8 | 113.1 | 300.0 |
| Dabi (ng/mL) | 50 | 45.3 | 149.3 | 41.9 | 11.6 | 47.6 | 184.8 |
|  | 150 | 72.3 | 244.5 | 54.7 | 13.0 | 76.0 | 300.0 |
|  | 300 | 95.1 | 300.0 | 68.3 | 14.9 | 88.9 | 300.0 |
|  | 600 | 105.6 | 300.0 | 84.7 | 20.2 | 100.0 | 300.0 |
| Riva (ng/mL) | 50 | 19.2 | 120.3 | 33.9 | 12.3 | 26.9 | 188.9 |
|  | 150 | 23.9 | 169.0 | 38.6 | 16.1 | 35.5 | 284.3 |
|  | 300 | 28.6 | 210.2 | 45.0 | 20.6 | 44.4 | 300.0 |
|  | 600 | 36.3 | 277.0 | 55.4 | 31.2 | 55.4 | 300.0 |
| Apixa (ng/mL) | 50 | 20.0 | 101.4 | 31.1 | 11.5 | 26.4 | 148.4 |
|  | 150 | 23.6 | 141.4 | 33.2 | 12.7 | 33.0 | 236.2 |
|  | 300 | 26.7 | 174.4 | 34.7 | 14.8 | 38.2 | 300.0 |
|  | 600 | 31.3 | 225.6 | 38.7 | 19.3 | 46.6 | 300.0 |

Figure 5.

|  |  | A | B | C | D | E | F |
|---|---|---|---|---|---|---|---|
| NPP | 0.0 | 24.6 | 52.8 | 29.3 | 10.8 | 26.2 | 82.9 |
| Hirudin (µg/mL) | 0.4 | 59.3 | 300.0 | 54.9 | 12.0 | 65.6 | 300.0 |
|  | 1.5 | 139.9 | 300.0 | 75.9 | 13.8 | 165.0 | 300.0 |
|  | 2.5 | 210.9 | 300.0 | 84.9 | 15.0 | 270.0 | 300.0 |
|  | 3.0 | 241.4 | 300.0 | 88.5 | 15.6 | 300.0 | 300.0 |
| Argatroban (µg/mL) | 0.3 | 79.8 | 174.9 | 50.7 | 13.9 | 70.7 | 300.0 |
|  | 1.0 | 108.3 | 287.5 | 70.3 | 22.0 | 95.5 | 300.0 |
|  | 1.5 | 118.4 | 300.0 | 79.0 | 28.1 | 105.2 | 300.0 |
|  | 2.0 | 126.4 | 300.0 | 85.8 | 32.8 | 113.1 | 300.0 |
| Dabi (ng/mL) | 50 | 45.3 | 149.3 | 41.9 | 11.6 | 47.6 | 184.8 |
|  | 150 | 72.3 | 244.5 | 54.7 | 13.0 | 76.0 | 300.0 |
|  | 300 | 95.1 | 300.0 | 68.3 | 14.9 | 88.9 | 300.0 |
|  | 600 | 105.6 | 300.0 | 84.7 | 20.2 | 100.0 | 300.0 |
| Riva (ng/mL) | 50 | 19.2 | 120.3 | 33.9 | 12.3 | 26.9 | 188.9 |
|  | 150 | 23.9 | 169.0 | 38.6 | 16.1 | 35.5 | 284.3 |
|  | 300 | 28.6 | 210.2 | 45.0 | 20.6 | 44.4 | 300.0 |
|  | 600 | 36.3 | 277.0 | 55.4 | 31.2 | 55.4 | 300.0 |
| Apixa (ng/mL) | 50 | 20.0 | 101.4 | 31.1 | 11.5 | 26.4 | 148.4 |
|  | 150 | 23.6 | 141.4 | 33.2 | 12.7 | 33.0 | 236.2 |
|  | 300 | 26.7 | 174.4 | 34.7 | 14.8 | 38.2 | 300.0 |
|  | 600 | 31.3 | 225.6 | 38.7 | 19.3 | 46.6 | 300.0 |

Figure 6.

|  |  | A | B | C | D | E | F |
|---|---|---|---|---|---|---|---|
| NPP | 0.0 | 24.6 | 52.8 | 29.3 | 10.8 | 26.2 | 82.9 |
| Hirudin (µg/mL) | 0.4 | 59.3 | 300.0 | 54.9 | 12.0 | 65.6 | 300.0 |
|  | 1.5 | 139.9 | 300.0 | 75.9 | 13.8 | 165.0 | 300.0 |
|  | 2.5 | 210.9 | 300.0 | 84.9 | 15.0 | 270.0 | 300.0 |
|  | 3.0 | 241.4 | 300.0 | 88.5 | 15.6 | 300.0 | 300.0 |
| Argatroban (µg/mL) | 0.3 | 79.8 | 174.9 | 50.7 | 13.9 | 70.7 | 300.0 |
|  | 1.0 | 108.3 | 287.5 | 70.3 | 22.0 | 95.5 | 300.0 |
|  | 1.5 | 118.4 | 300.0 | 79.0 | 28.1 | 105.2 | 300.0 |
|  | 2.0 | 126.4 | 300.0 | 85.8 | 32.8 | 113.1 | 300.0 |
| Dabi (ng/mL) | 50 | 45.3 | 149.3 | 41.9 | 11.6 | 47.6 | 184.8 |
|  | 150 | 72.3 | 244.5 | 54.7 | 13.0 | 76.0 | 300.0 |
|  | 300 | 95.1 | 300.0 | 68.3 | 14.9 | 88.9 | 300.0 |
|  | 600 | 105.6 | 300.0 | 84.7 | 20.2 | 100.0 | 300.0 |
| Riva (ng/mL) | 50 | 19.2 | 120.3 | 33.9 | 12.3 | 26.9 | 188.9 |
|  | 150 | 23.9 | 169.0 | 38.6 | 16.1 | 35.5 | 284.3 |
|  | 300 | 28.6 | 210.2 | 45.0 | 20.6 | 44.4 | 300.0 |
|  | 600 | 36.3 | 277.0 | 55.4 | 31.2 | 55.4 | 300.0 |
| Apixa (ng/mL) | 50 | 20.0 | 101.4 | 31.1 | 11.5 | 26.4 | 148.4 |
|  | 150 | 23.6 | 141.4 | 33.2 | 12.7 | 33.0 | 236.2 |
|  | 300 | 26.7 | 174.4 | 34.7 | 14.8 | 38.2 | 300.0 |
|  | 600 | 31.3 | 225.6 | 38.7 | 19.3 | 46.6 | 300.0 |

Figure 7.
(A)

| | | A | B | C | D | E | F |
|---|---|---|---|---|---|---|---|
| NPP | 0.0 | 24.6 | 52.8 | 29.3 | 10.8 | 26.2 | 82.9 |
| UFH (IU/mL) | 0.3 | 60.2 | 220.1 | 54.8 | 10.9 | 28.4 | 80.6 |
| | 0.8 | 106.5 | 300.0 | 186.7 | 11.5 | 26.5 | 68.4 |
| LMWH (IU/mL) | 0.4 | 69.1 | 300.0 | 44.0 | 11.0 | 27.4 | 81.4 |
| | 1.0 | 114.7 | 300.0 | 81.3 | 11.5 | 26.1 | 43.5 |
| Fonda (μg/mL) | 0.3 | 53.8 | 123.3 | 31.8 | 11.1 | 31.1 | 80.6 |
| | 1.3 | 78.7 | 300.0 | 34.1 | 11.6 | 49.5 | 94.7 |
| Hirudin (μg/mL) | 0.4 | 59.3 | 300.0 | 54.9 | 12.0 | 65.6 | 300.0 |
| | 2.5 | 210.9 | 300.0 | 84.9 | 15.0 | 270.0 | 300.0 |
| Arga (μg/mL) | 0.3 | 79.8 | 174.9 | 50.7 | 13.9 | 70.7 | 300.0 |
| | 1.5 | 118.4 | 300.0 | 79.0 | 28.1 | 105.2 | 300.0 |
| Dabi (ng/mL) | 50 | 45.3 | 149.3 | 41.9 | 11.6 | 47.6 | 184.8 |
| | 300 | 95.1 | 300.0 | 68.3 | 14.9 | 88.9 | 300.0 |
| Riva (ng/mL) | 50 | 19.2 | 120.3 | 33.9 | 12.3 | 26.9 | 188.9 |
| | 300 | 28.6 | 210.2 | 45.0 | 20.6 | 44.4 | 300.0 |
| Apixa (ng/mL) | 50 | 20.0 | 101.4 | 31.1 | 11.5 | 26.4 | 148.4 |
| | 300 | 26.7 | 174.4 | 34.7 | 14.8 | 38.2 | 300.0 |

Figure 7. cont.
(B)

|  |  | A | B | C | D | E | F |
|---|---|---|---|---|---|---|---|
| Plasma | 0.0 | 26.4 | 35.0 | 26.5 | 11.5 | 25.0 | 59.8 |
| UFH (IU/mL) | 0.3 | 75.9 | 161.7 | 59.8 | 11.9 | 26.1 | 51.4 |
|  | 0.8 | 118.4 | 300.0 | 184.0 | 12.2 | 26.7 | 49.5 |
| LMWH (IU/mL) | 0.4 | 77.2 | 139.2 | 43.4 | 11.6 | 26.9 | 50.5 |
|  | 1.0 | 121.2 | 300.0 | 69.4 | 11.7 | 26.3 | 44.1 |
| Fonda (μg/mL) | 0.3 | 48.6 | 57.8 | 29.5 | 11.8 | 28.7 | 57.4 |
|  | 1.3 | 76.0 | 151.8 | 31.4 | 12.1 | 39.3 | 53.4 |
| Hirudin (μg/mL) | 0.4 | 68.7 | 300.0 | 47.7 | 12.7 | 62.9 | 300.0 |
|  | 2.5 | 228.9 | 300.0 | 74.1 | 15.4 | 215.9 | 300.0 |
| Arga (μg/mL) | 0.3 | 96.2 | 159.6 | 49.9 | 16.2 | 79.7 | 278.7 |
|  | 1.5 | 146.2 | 300.0 | 82.2 | 33.5 | 120.4 | 300.0 |
| Dabi (ng/mL) | 50 | 52.2 | 108.6 | 35.8 | 12.5 | 47.7 | 216.6 |
|  | 300 | 108.2 | 300.0 | 57.9 | 15.7 | 95.1 | 300.0 |
| Riva (ng/mL) | 50 | 18.4 | 89.4 | 31.3 | 13.4 | 22.2 | 133.5 |
|  | 300 | 27.8 | 170.7 | 42.5 | 22.7 | 35.3 | 261.3 |
| Apixa (ng/mL) | 50 | 18.4 | 65.4 | 28.4 | 12.3 | 20.1 | 110.6 |
|  | 300 | 23.9 | 126.7 | 32.4 | 15.8 | 29.1 | 202.4 |

Figure 7. cont.
(C)

|  |  | A | B | C | D | E | F |
|---|---|---|---|---|---|---|---|
| NPP |  | 24.6 | 52.8 | 29.3 | 10.8 | 26.2 | 82.9 |
| UFH (IU/mL) | 0.3 | 60.2 | 220.1 | 54.8 | 10.9 | 28.4 | 80.6 |
|  | 0.8 | 106.5 | 300.0 | 186.7 | 11.5 | 26.5 | 68.4 |
| LMWH (IU/mL) | 0.4 | 69.1 | 300.0 | 44.0 | 11.0 | 27.4 | 81.4 |
|  | 1.0 | 114.7 | 300.0 | 81.3 | 11.5 | 26.1 | 43.5 |
| Fonda (μg/mL) | 0.3 | 53.8 | 123.3 | 31.8 | 11.1 | 31.1 | 80.6 |
|  | 1.3 | 78.7 | 300.0 | 34.1 | 11.6 | 49.5 | 94.7 |
| Hirudin (μg/mL) | 0.4 | 59.3 | 300.0 | 54.9 | 12.0 | 65.6 | 300.0 |
|  | 2.5 | 210.9 | 300.0 | 84.9 | 15.0 | 270.0 | 300.0 |
| Arga (μg/mL) | 0.3 | 79.8 | 174.9 | 50.7 | 13.9 | 70.7 | 300.0 |
|  | 1.5 | 118.4 | 300.0 | 79.0 | 28.1 | 105.2 | 300.0 |
| Dabi (ng/mL) | 50 | 45.3 | 149.3 | 41.9 | 11.6 | 47.6 | 184.8 |
|  | 300 | 95.1 | 300.0 | 68.3 | 14.9 | 88.9 | 300.0 |
| Riva (ng/mL) | 50 | 19.2 | 120.3 | 33.9 | 12.3 | 26.9 | 188.9 |
|  | 300 | 28.6 | 210.2 | 45.0 | 20.6 | 44.4 | 300.0 |
| Apixa (ng/mL) | 50 | 20.0 | 101.4 | 31.1 | 11.5 | 26.4 | 148.4 |
|  | 300 | 26.7 | 174.4 | 34.7 | 14.8 | 38.2 | 300.0 |

Figure 7. cont.
(D)

|  |  | A | B | C | D | E | F |
|---|---|---|---|---|---|---|---|
| Plasma | 0.0 | 32.9 | 36.4 | 32.8 | 9.9 | 36.2 | 45.4 |
| UFH (IU/mL) | 0.3 | 81.2 | 130.3 | 74.0 | 10.4 | 37.9 | 35.6 |
|  | 0.8 | 119.7 | 300.0 | 207.5 | 10.5 | 37.2 | 32.4 |
| LMWH (IU/mL) | 0.4 | 85.2 | 118.5 | 52.5 | 10.1 | 38.3 | 35.6 |
|  | 1.0 | 125.3 | 300.0 | 94.4 | 10.4 | 38.4 | 30.1 |
| Fonda (µg/mL) | 0.3 | 59.0 | 55.3 | 36.9 | 10.1 | 41.8 | 41.6 |
|  | 1.3 | 93.4 | 126.0 | 38.7 | 10.7 | 54.5 | 42.3 |
| Hirudin (µg/mL) | 0.4 | 109.0 | 300.0 | 73.4 | 10.8 | 116.1 | 300.0 |
|  | 2.5 | 300.0 | 300.0 | 143.4 | 13.0 | 300.0 | 300.0 |
| Arga (µg/mL) | 0.3 | 100.7 | 135.1 | 73.5 | 13.7 | 91.5 | 189.0 |
|  | 1.5 | 154.4 | 300.0 | 130.1 | 28.8 | 132.3 | 300.0 |
| Dabi (ng/mL) | 50 | 71.3 | 108.9 | 45.0 | 10.5 | 71.7 | 171.5 |
|  | 300 | 126.8 | 256.1 | 93.8 | 13.1 | 112.4 | 300.0 |
| Riva (ng/mL) | 50 | 19.7 | 87.0 | 39.1 | 11.2 | 25.5 | 113.7 |
|  | 300 | 30.7 | 153.5 | 56.6 | 17.8 | 41.1 | 203.2 |
| Apixa (ng/mL) | 50 | 20.1 | 62.9 | 33.8 | 10.3 | 25.9 | 80.3 |
|  | 300 | 25.8 | 121.9 | 40.4 | 13.1 | 34.7 | 157.3 |

IDENTIFICATION OF ANTICOAGULANTS IN A SAMPLE

CROSS-REFERENCE TO RELATED APPLICATIONS

This application is a continuation of Ser. No. 15/102,944, filed Jun. 9, 2016, now abandoned, which is a U.S. National Phase of PCT Application No. PCT/EP2014/077084, filed Dec. 9, 2014, which designated the U.S and claims priority to CH Patent Application No. CH02038/13, filed Dec. 9, 2013, each of which is incorporated herein by reference in its entirety.

BACKGROUND OF THE INVENTION

The present invention is directed to a novel method of determining inhibitors of proteolytically active coagulation factors, referred to herein as anticoagulants, in a sample, in particular the qualitative detection of direct thrombin and factor Xa inhibitors in a sample. The method of the present invention allows a qualitative determination of the nature anticoagulants present in a sample. This can be achieved with only one coagulation-based test. The method can be used in a test kit, including a point-of-care (POC) system.

The so-called coagulation cascade as part of the secondary hemostasis consists of the contact activation pathway (also known as the intrinsic pathway) and the tissue factor pathway (also known as extrinsic pathway) leading to fibrin formation. In the tissue factor pathway, damaged tissue exposes tissue factor which activates factor VII to its activated form VIIa. Tissue factor and factor VIIa form a complex which activates factor X at the common pathway. In the contact pathway, negatively charged surfaces are exposed to the action of factor XII and prekalikrein in the blood. The activated factor XIIa activates factor XI to factor XIa. Factor XIa activates factor IX to the activated form IXa. Factor IXa, VIIIa, phospholipids and free calcium ions are required for the formation of the tenase complex, which activates factor X to become factor Xa. The formation of the prothrombinase complex is performed via action of factors Xa, Va, phospholipids and free calcium ions. Said prothrombinase complex activates the formation of thrombin from prothrombin.

For the past 50 years vitamin K antagonists (VKAs) were the only available therapeutic solution for long-term anticoagulation in patients with chronic thromboembolic risk. VKA treatment requires regular monitoring which represents a major disadvantage for the patient.

In many situations including short-term treatment, different strategies for rapid anticoagulation are necessary. One strategy for attaining anticoagulation in patients is the direct or indirect inhibition of activated coagulation factors using heparins and heparinoids, which require antithrombin factor III or heparin cofactor II from plasma, direct natural or synthetic inhibitors of factor IIa and Xa. Examples are heparins, either unfractionated heparin (UFH), the sodium salt or low molecular weight heparins (LMWHs), including but not limited to enoxaparin or its sodium salt (marketed as e.g. Lovenox®, Clexane®, Xaparin®), dalteparin or its sodium salt (marketed as e.g. Fragmin®), tinzaparin or its sodium salt (marketed as e.g. Innohep®), nadroparin (marketed as e.g. Fraxiparin®), certoparin (marketed as e.g. Sandoparin®, Mono-Embolex®), reviparin (marketed as e.g. Clivarin®).

Other thrombin inhibitors include hirudin, a natural polypeptide of 65 amino acids, which is used as therapeutic agent in the form of bivalhirudin (marketed as e.g. Angiox®) or lepirudin (marketed as e.g. Refludan®); argatroban, a derivative of arginine (marketed as e.g. Argatra®); or the tick anticoagulants.

Fondaparinux or its sodium salt (marketed as e.g. Arixtra®) is known as indirect factor Xa inhibitor, which is a synthetic pentasaccharide, with some advantages over heparins or hirudins.

Except for the VKAs, all these drugs have to be administered parenteral, i.e. via infusion, injection or implantation, which makes them mostly only used for medical treatment in hospitals, e.g. in connection with a medical surgery.

Since 2000, so-called new or direct oral anticoagulants (NOACs/DOACs) have been developed to alleviate the need for recurrent monitoring and for better handling outside the hospital environment. These NOACs play an increasingly important role in the prevention and/or treatment of cardiovascular or thromboembolic disorders. There are currently three NOACs (rivaroxaban, apixaban and dabigatran) in the market and new ones are expected in the near future.

NOACs act as direct anticoagulants, i.e. inhibitors of the central procoagulatory factors of the blood coagulation system. They include inhibitors of factor IIa (thrombin), such as dabigatran or dabigatran etexilate (marketed as e.g. Pradaxa®, Prazaxa®, Pradax®) and inhibitors of factor Xa, such as rivaroxaban (marketed as e.g. Xarelto®), apixaban (marketed as e.g. Eliquis®), edoxaban (marketed as e.g. Lixiana®), betrixaban or otamixaban.

There are several standard assays available to measure the effect of coagulation and/or the concentration of such drugs in a sample such as blood or plasma. These coagulation-based tests consist of a reagent which triggers the coagulation cascade in a sample such as, e.g., blood or plasma, in order to induce clot formation. The time required for clot formation in said sample (so-called clotting time; CT) is measured by an operator. The presence of an anticoagulant in said sample can in certain instances lead to a delay in the time required for coagulation depending on the nature of the test and its level of responsiveness to a particular anticoagulant. The skilled person knows these test methods, most of them being described in e.g. EP1240528 (incorporated herein by reference).

Measurement of the activated partial thrombin time (aPTT) and the prothrombin time (PT) are examples of readily available coagulation-based tests which response is affected by the presence of an anticoagulant in a sample, for example, blood or plasma. Whereas the PT or international normalized ratio (INR) is used as standard assay for measurement of VKA levels, aPTT is normally used for measuring the level of UFH and hirudin.

For some of the routinely used coagulation tests, such as e.g. PT or aPTT, it is known that they inefficiently respond to some anticoagulants, in particular with regards to quantitative measurement. With the prothrombinase-induced clotting time (PiCT®) assay a coagulation-based test is available with efficient response to the presence of most anticoagulant in a sample such as, e.g., blood or plasma. More specifically, PiCT® is known to efficiently respond in a quantitative manner to the presence of all known antithrombin and anti-Xa anticoagulants (see e.g. Calatzis, Haemostasis 2000, 30:172-174; Calatzis et al., Am J Clin Pathol 2008, 130:446-454). Another test method, the so-called ecarin clotting time (ECT) is responding to the presence of hirudin in a sample. An amidolytic assay is known to respond to e.g. UFHs, LMWH or fondaparinux. All these coagulation-based tests are known by the skilled in the art to be useful for analysis of the effect of an anticoagulant but only once the presence and nature of an anticoagulant is known. (see e.g. EP 1240528 or Korte et al., Hämostaseologie 30, 212-216, 2010).

Although routine monitoring of the level of NOACs in the blood of patients is not recommended by drug manufacturers, NOACs have created considerable concern in hemostasis laboratories since their introduction into clinical practice due to the lack of appropriate patient management tools or the lack of specific antidotes. Cases of major bleeding under NOAC therapy have been already reported. The need for measuring the anticoagulant effects of NOACs is still debated among experts. There are some clinical conditions where testing for these agents would be desirable or even life-saving. This is extremely important in an emergency situation dealing with patients with bleeding or at risk of bleeding when an invasive procedure is needed, in case of overdosing or if a patient has developed renal failures or the like. Thus, the physician has to know whether and in the affirmative which drug or at least which class of drug has been taken in order to decide on immediate measures, including the use of the right antidote. It is also important to note that some assays give different results depending on the concentration of the anticoagulant, such as NOACs in the sample. For this assessment, a reliable test system would be also desirable, in particular with regards to a POC system.

Some tests exist to measure specific anticoagulant concentrations thanks to calibration curves. Since there are no established therapeutic ranges to which associate appropriate therapy to, the usefulness of these curves can only be demonstrated upon association to clinically relevant situations. Thus, these tests may only be used for monitoring and only once the presence of the drug is known. On the other hand, there are no tests available allowing to detect the presence of NOACs in samples such as e.g. plasma or blood to identify the nature of the anticoagulant drug if present. Adaptations of existing routine hemostasis tests, e.g. (dTT), ECT, aPTT or thrombin time (TT), aimed to assess global coagulation status or anticoagulant effect of other anticoagulant drugs failed to provide optimal solution to physicians for patients treated with NOACs.

Thus, there is a need for a readily available, easy performable and reliable testing method which could provide information of the presence of an anticoagulant, in particular with regards to NOACs, in a sample, within a short period of time, including use in a POC system. Further there is a need for a testing method which could enable identification of the nature of such drugs, in particular with regards to NOACs in the sample such as e.g. human blood or plasma. Particularly in the case of NOACs, this method should provide either qualitative and quantitative information to the testing person, e.g. the physician or the patient him/herself.

BRIEF SUMMARY OF THE INVENTION

Surprisingly, we have now found a method wherein the presence of an anticoagulant in a sample is qualitatively determined using a single coagulation-based test. Moreover, the use of said single coagulation-based test enables the tester to determine the presence of various kinds of anticoagulants such as, for example, antithrombin or anti-Xa anticoagulants in a sample, such as, e.g., human blood or plasma. For confirmation of the results, said single coagulation test can be used in combination with other known assays, e.g. PT or aPTT, to further identify the nature of an anticoagulant present in a sample, in particular in human blood or plasma. This method is in particular useful for identification of NOACs in a sample.

One important feature of such test system is the PiCT® technology, in particular the Pefakit® PiCT® test, which is sensitive to all factor Xa and factor IIa inhibiting drugs. Contrary to standard routine tests of limited specific use, Pefakit® PiCT® counts with the potential of relying on a single test in order to address all clinical needs related to assessment of anticoagulant therapies. The system has been specifically adapted for this purpose. PiCT® is either used as disclosed in EP 1240528 or slightly adapted for certain drugs, in particular adapted as so-called inverted PiCT® as further explained herein, which is in particular useful for identification of NOACs. The novel and inventive method is based on a surprising overreaction or underreaction of the test to certain anticoagulants when utilized making use of a particular methodology. Furthermore, the use of this same principle in combination with other coagulation-based tests such as, for example, but not limited to, aPTT and/or PI, allows for further determination/confirmation of the nature of the anticoagulant present in a sample, such as e.g. human blood or plasma.

This is the first time that identification of the presence of an anticoagulant, i.e. yes/no using only one test, i.e. the PiCT® system, and identification of the nature of the anticoagulant using only one test is possible. Furthermore, we present here for the first time a system wherein NOACs can be identified by application of only one single test system.

BRIEF DESCRIPTION OF THE DRAWINGS

FIG. 2. Evaluation of a sample wherein fondaparinux is present. Values out of range are in bold, values in the RR are indicated with a grey background color, borderline values are in Italic. The anticoagulants are listed in the right-hand column, with UFH, LMWH, Fonda (fondaparinux), hirudin, argatroban, Dabi (dabigatran), Riva (rivaroxaban), Apixa (apixaban). NPP without any anticoagulants is used as control. The columns are as follows: (A)=standard PiCT®, (B)=inverted PiCT®, (C)=aPTT, (D)=PT; (E)=polybrene standard PiCT®, (F)=polybrene inverted PiCT®.

FIG. 3. Evaluation of a sample wherein either UFH, LMWH, hirudin or low concentration of dabigatran is present. Values out of range are in bold, values in the RR are indicated with a grey background color, borderline values are in Italic. For more detail see text or legend to FIG. 2.

FIG. 4. Confirmation of results shown in FIG. 3 for UFH and LMWH. For more detail see text of legend to FIG. 2.

FIG. 5. Evaluation of a sample wherein rivaroxaban or apixaban is present. For more detail see text or legend to FIG. 2.

FIG. 6. Evaluation of a sample wherein hirudin, argatroban or dabigatran is present. For more details see text or legend to FIG. 2.

FIG. 7. In order to test the method for feasibility under real-life conditions and to evaluate its use in a point-of-care (POC) system, individual plasma samples were tested with the combination of assays (see legend to FIG. 2). For each patient, two separate runs were performed. The results are shown in panels (A) and (B) for patient 1 and panels (C) and (D) for patient 2.

DETAILED DESCRIPTION OF THE INVENTION

Figure 1:
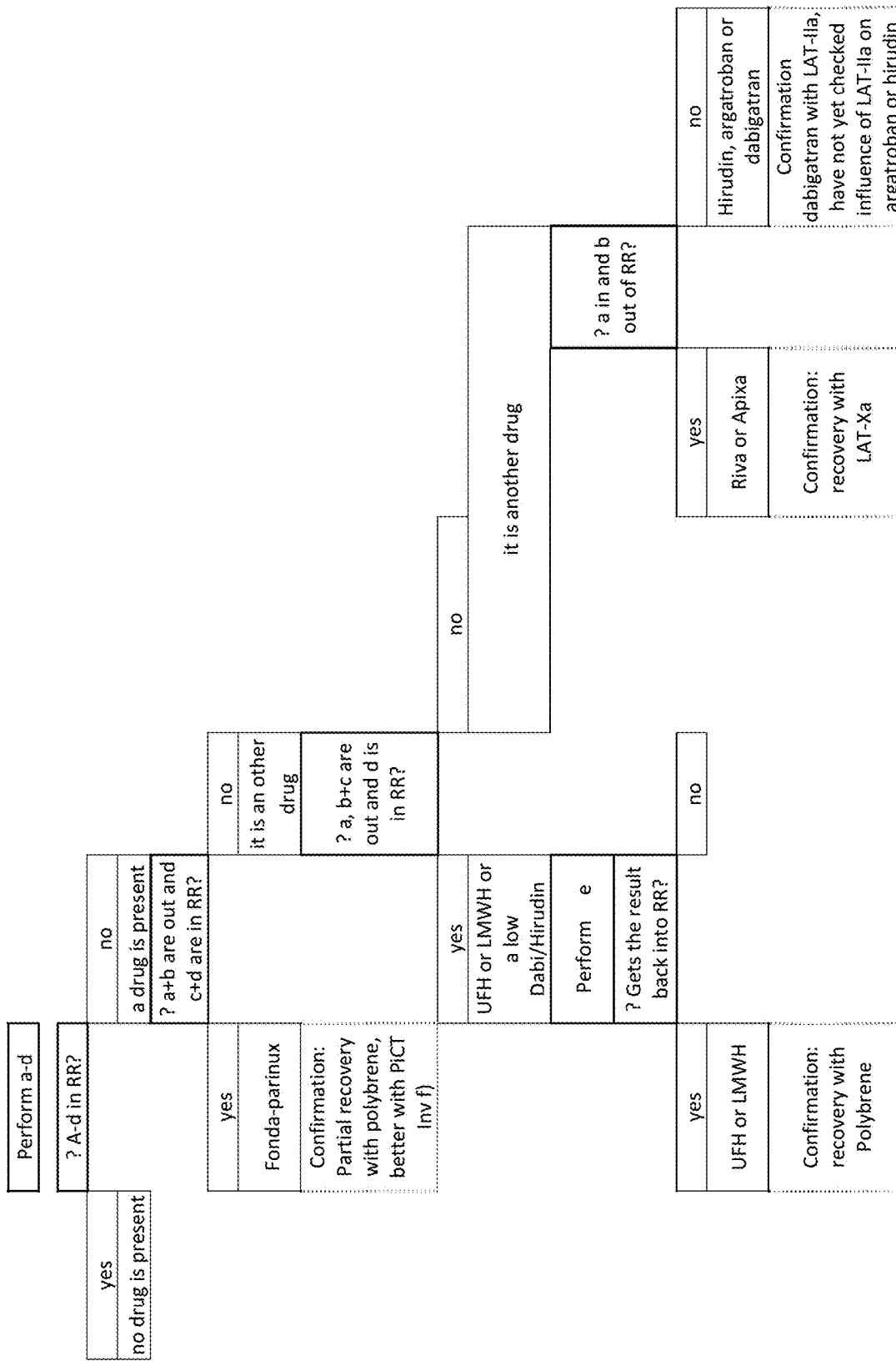
FIG. 1. Flow diagram for the identification different anticoagulants in a sample, e.g. blood or plasma, using PiCT® Method 1 (a), PiCT® Method 2 (b), PiCT® Method 3 (c), PiCT® Method 4 (d) using the ACL TOP® 500 analyzer. The method comprises analyzing the sample using PiCT® Methods 1 to 4 and determining whether the values obtained using the various PiCT® Methods are inside or outside the relevant Reference Range. For example, "Perform a-d" is the instruction to analyze the sample using PiCT® Methods 1 to 4, and "? A-d in RR?" stands for the instruction to determine whether the values obtained for the sample are inside of the relevant Reference Ranges ("RR"). "e" stands for polybrene standard PiCT®, and "f" stands for polybrene inverted PiCT®.

PiCT® can be used for monitoring the level of all known anticoagulants which are directly inhibitors of factor Xa and/or factor IIa, in particular used for monitoring the level of UFH, LMWH, hirudin, fondaparinux, argatroban, and NOACs, preferably, dabigatran, rivaroxaban, and apixaban.

A sample as used herein includes fluids taken from a human or animal, in particular fluids taken from humans, such as e.g. whole blood or plasma containing the anticoagulant to be analyzed or monitored. The present invention is capable of determining whether an anticoagulant is present at all in said sample and in the affirmative, the tester can determine which drug or class of drug is present in the sample.

As used herein, the terms "drug" and "anticoagulant" are used interchangeably.

As used herein, the terms Pefakit® PiCT® and PiCT® are used interchangeably. Pefakit® PiCT® is a diagnostic kit available from DSM Nutritional Products Branch Pentapharm, Switzerland which makes use of the PiCT® technology.

As described by Korte et al. (supra) or in EP 1240528, Pefakit® PiCT® is a functional clotting assay based on the direct activation of the prothrombinase complex which results in a fine-tuned analytical output directly proportional to the final anticoagulant activity of the factor Xa or factor IIa inhibitors (see Calatzis, Haemostasis 2000, 30:172-174). To perform the Pefakit® PiCT® test (referred to herein as standard "PiCT® or PiCT® Method 1), a defined amount of PiCT® activator (=reagent 1) is added to a sample, such as, e.g., plasma. The mixture is allowed to proceed at 37° C. for a specific period of time. The Start reagent (=reagent 2) is then added to the mixture and the time required for clot formation is measured. The presence of anticoagulants in the samples dose-dependently prolongs the time to clot. Pefakit® PiCT® is adapted to laboratory instruments based on mechanical or optical detection systems, including but not limited to ACL TOP® family (Instrumentation Laboratory), preferably ACL TOP® 500, STA Compact® series (Stago) or the BCS® XP series (Siemens).

Thus, in one aspect, the present invention comprises adding to the sample, in particular selected from human blood or plasma, the reagents and all compounds needed for the reaction to occur, thus creating a reaction mixture. This reaction mixture is the subject of detection. The reaction mixture can be provided during the detection part of the method, but preferably is done prior to the start of the detection. Adaptation is made with regards to the amount of sample, the amount of reagents, the reaction time, and/or, the order of reagents to be added as described in more detail herein.

For correct interpretation of the results, specific sets of values or reference ranges (RR) are used which are adapted to the detection system, e.g. the coagulometer, and the kind of testing method, such as e.g., PT, aPTT or PiCT®. The skilled person knows how to establish these RR for the different detection systems in connection with the testing method used, e.g., PT, aPTT or PiCT® testing method. In case the value tested in a sample is out of range, the tester knows that the sample contains anticoagulants. An example of such a measurement of RR is shown in Table 1, wherein the settings are adapted for the ACL TOP® 500 (Instrumentation Laboratory).

If the measurements are performed with another instrument known to the skilled person, the RR have to be determined accordingly, i.e. specific pipetting schemes have to be designed in order to achieve high reproducibility in the sample including plasma from healthy donors and normal plasma pool (NPP) spiked with incremental amounts of anticoagulants. After determination of the RR, the best dose response curves (DRCs) for each drug have to be defined for each drug and/or each detection system. These procedures are known in the art.

TABLE 1

PiCT ®, aPTT and PT adaptation and RR measured on ACL TOP ® 500. Values are indicated in seconds. "Out" means out of range, i.e. extension of the clotting time due to presence of anticoagulants in the sample. For more details see text.

| Method | RR | Borderline | Out |
|---|---|---|---|
| PiCT ® standard | 21.4-36.2 | 36.3-39.8 | 39.9-300 |
| PiCT ® fondaparinux | 32.1-68.2 | 68.3-75.0 | 75.1-300 |
| PiCT ® dabigatran | 35.1-76.6 | 76.7-84.3 | 84.4-300 |
| PiCT ® inverted | 21.9-106.4 | 106.5-117.0 | 117.1-300 |
| aPTT | 25.4-36.9 | 37.0-40.6 | 40.7-300 |
| PT | 9.4-12.5 | 12.5-13.8 | 13.9-100 |

The present invention is in one aspect directed to the use of a clotting assay, in particular the PiCT® testing method on a detection system such as e.g. the ACL TOP® 500 analyzer and to a method to quantitatively and qualitatively detect anticoagulants in a sample, e.g. blood or plasma. Particularly, 4 different/adapted methods based on standard PiCT® (i.e. PiCT® Method 1) have been developed to achieve the best DRCs for all types of anticoagulants—except for anticoagulants of the VKA type—such as in particular for anticoagulants selected from UFH, LMWH, hirudin, fondaparinux, argatroban and NOACs including dabigatran, rivaroxaban and apixaban. Thus, for identification of drugs like fondaparinux the PiCT® Method 2 is in particularly useful, including a modified/adapted pipetting scheme compared to the standard procedure. The same turned out to be useful for dabigatran or argatroban (=PiCT® Method 3), wherein another modified/adapted pipetting scheme is used or for NOACs such as e.g. rivaroxaban or apixaban (=PiCT® Method 4). PiCT® Method 4 or PiCT® inverted includes that first the start reagent is added to the sample, the mixture allowed to proceed according to the manufacturer's instructions followed by addition of the activator, i.e. a reversed order compared to standard PiCT® (see above). PiCT® Method 1 to 4 is described in more detail in the Examples.

The 4 methods (see above) are in more detail described in the Examples. Specific pipetting schemes were designed using NPP spiked with incremental amounts of anticoagulants in order to achieve high reproducibility of the test system, which is required for drug identification including use in a POC system. With regards to the ACL TOP® 500 analyzer, PiCT® Method 1 to 4 has been established as follows:

PiCT® Method 1: 50 µl of plasma is incubated for 180 sec with 50 µl of reagent 1 and afterwards 50 µl of reagent 2 is added and the time to clot is recorded on the ACL TOP® 500 (i.e. pipetting scheme: P-50/A-50/I-180/50-S). This method is in particularly useful for detection of UFH, LMWH or hirudin.

PiCT® Method 2: P-75/A-65/I-180/35-S on the ACL TOP® 500 or P-80/A-65/I-180/40-S on the STA Compact® or P-75/A-65/I-180/S-40 on the BCS® XP. This method is in particularly useful for fondaparinux.

PiCT® Method 3: P-90/A-70/I-180/40-S on the ACL TOP® 500 or STA Compact®, or P-70/A-60/I-180/45-S on the BCS® XP. This method is in particularly useful for dabigatran or argatroban.

PiCT® Method 4: P-140/S-45/I160/A-40 on the ACL TOP® 500 or STA Compact®, or P-125/S-45/I-150/A-40 on the BCS® XP. This method is in particularly useful for rivaroxaban or apixaban.

Thus, in one aspect the present invention is directed to the use of PiCT® for identification of NOACs, in particular rivaroxaban or apixaban, in a sample, such as e.g. human blood or plasma, wherein the sample is first supplemented with the activator reagent, the mixture allowed to proceed and finally supplemented with the start reagent.

In one aspect, the present invention is directed to a method of measuring the presence of an anticoagulant in a sample, such as a fluid, in particular from human or animal, preferably blood or plasma. Thus, the physician/patient, i.e. the tester, needs to know whether or not an anticoagulant is present in e.g. a blood or plasma sample. A first evaluation is done by standard PiCT® testing (PiCT® Method 1): a measurement of clotting times out of range, i.e. above the RR, indicates the presence of UFH, LMWH, hirudin, argatroban, fondaparinux or dabigatran in the sample. With regards to NOACs such as rivaroxaban or apixaban, this Method 1, i.e. the standard PiCT®, is in the RR even if concentrations in the range of about 300 ng/ml are present in the sample. In the case of dabigatran, the clotting times measured with this method are above the RR, meaning out of range.

The detection of (low) levels of anticoagulants including NOACs in a sample is a further aspect of the present invention. The use of so-called inverted PiCT® testing method (see above) turned out to be a particular useful method for this purpose.

Examples of anticoagulants, preferably in low concentrations, which can be detected with said method (PiCT® Method 4) are selected from dabigatran, heparins such as e.g. UFH and LMWH, hirudin, fondaparinux, argatroban as well as the NOACs, e.g. rivaroxaban or apixaban. As used herein, a low concentration of anticoagulant means a range of 20 to 35 ng/ml with regards to rivaroxaban, apixaban or dabigatran, in the range of 0.3 to 0.4 µg/ml with regards to fondaparinux or argatroban or hirudin, in the range of 0.3 to 0.4 IU/ml with regards to heparins, such as e.g. UFH or LMWH.

Thus, for identification of drugs such as dabigatran, rivaroxaban or apixaban the inverted PiCT® testing method (referred herein as PiCT® Method 4) is used as detection test.

To determine whether the NOAC in the sample is dabigatran or the like, the first test, i.e. PiCT® Method 1 resulted in clotting times out of range, a second test is performed, wherein the inverted PiCT® described above, corresponding to PiCT® Method 4, together e.g. with the ACL TOP® 500 analyzer, can be used and a clotting time above the RR of about 21.4 to about 37.9, such as e.g. above about 29.6, means the presence of dabigatran in the sample. The RR measured with dabigatran (see above) using the standard PiCT® gives results out of range, which is in contrast to other NOACs such as rivaroxaban and apixaban. The particular clotting times measured for the different anticoagulants are shown in Table 2.

In one particular aspect, the present invention is directed to a method to determine which kind of anticoagulant is present in a sample, e.g. in particular whether the sample comprises an anticoagulant selected from the group consisting of UFH, LMWH, hirudin, fondaparinux, argatroban, dabigatran, rivaroxaban and apixaban, wherein the sample may be selected from a fluid, such as in particular from human or animal, preferably blood or plasma. This method basically is a combination of 4 tests, wherein first PiCT® Method 1 and 4 are performed, combined with aPTT and PT (for confirmation of the results) and the combined results, i.e. measured clotting times, are analyzed with the detection system such as e.g. the ACL TOP® 500 analyzer:

(1) If all 4 tests result in clotting times within the RR determined beforehand (see e.g. in Table 1 as established for the ACL TOP® 500 analyzer), there is no drug present in the sample.

(2) If PiCT® Method 1 is within the RR, but Method 4 gives results out of range (such as e.g. clotting times below about 24.4 to about 30.4, such as e.g. below about 27.6, and if the clotting times according to PiCT® Method 4 are above the RR of about 21.4 to about 37.9, such as e.g. above about 29.6 as established for the ACL TOP® 500 analyzer shown in Table 1), the sample contains NOACs selected from rivaroxaban or apixaban. Depending on the concentration, the PT and aPTT are either out of RR (i.e. PT out of RR with higher concentrations of both NOACs) or within the RR (i.e. aPTT within the RR with normal or lower concentration of both NOACs). This is in more detailed outlined in the Examples.

(3) If the modified PiCT®, i.e. PiCT® Method 3, as well as PiCT® Method 4 show clotting times out of range, the sample might contain either dabigatran or argatroban. These results would be confirmed with the PT and aPTT, i.e. clotting times also above RR. Only in case of low concentration of dabigatran, the PT shows clotting times within the RR.

(4) If the standard PiCT®, i.e. PiCT® Method 1, as well as PiCT® Method 4 show clotting times out of range, the sample might contain either UFH, LMWH or hirudin. Whereas the aPTT might be also out of range for all three anticoagulants, PT will be out of range only for hirudin, but within the RR for UFH, LMWH or low concentration of hirudin.

(5) If the modified PiCT®, i.e. PiCT® Method 2, as well as PiCT® Method 4 is out of range, the sample might contain fondaparinux. In this case, PT and aPTT show clotting times within RR.

By the addition of polybrene a distinction can be done, which of the anticoagulants is really present in the sample: if after addition of polybrene the measured clotting times are again back to RR when using the PiCT® Method 1, the sample comprises heparins, such as e.g. UFH or LMWH. Alternatively, if the result is not going back to RR, the sample comprises low concentrations of dabigatran or hirudin. Similar results are obtained with NOACs like rivaroxaban or apixaban in the sample: after addition of polybrene the measured clotting times are out of range when using the PiCT® Method 1 (instead of within the RR without the addition of polybrene). However, in case of low concentrations of rivaroxaban or apixaban in the sample, the addition of polybrene has no effect on the clotting times. The particular clotting times measured for the different anticoagulants are shown in Table 6, which is an example of results obtained in spiked plasma samples.

In one particular embodiment, the present invention relates to a method for quantification the effect of anticoagulants in a sample, wherein the sample may be selected from a fluid, such as in particular from human or animal, preferably blood or plasma. In particular, the PiCT® Method 1 can be used to detect the effect of hirudin or heparins such as e.g. UFH and LMWH, together with e.g. the ACL TOP® 500 analyzer. Thus, first the sample such as e.g. plasma, in particular 50 µl of plasma, is incubated, in particular for 180 sec, with the reagent 1, in particular 50 µl, and afterwards the reagent 2, in particular 50 µl, is added and the time to clot is recorded as described above. The particular clotting times measured for UFH, LMWH or hirudin shown in Table 7 are examples of results obtained in spiked NPP samples.

If the effect of fondaparinux in a sample is to be quantified, a method similar to PiCT® Method 1 is used, referred herein and in Table 3 as PiCT® Method 2, together with e.g. the ACL TOP® 500 analyzer, i.e. first the sample such as e.g. plasma, in particular 75 µl, is incubated, in particular for 180 sec, with the reagent 1, in particular 65 µl, and afterwards the reagent 2, in particular 35 µl, is added and the time to clot is recorded, i.e. DRC. The particular clotting times measured for fondaparinux shown in Table 8 are examples of results obtained in spiked NPP samples.

In the case of dabigatran or argatroban, i.e. the determination of the quantitative effect of said drug in a sample, a method similar as described above and referred herein and in Table 3 as PiCT® Method 3, may be used together with e.g. the ACL TOP® 500 analyzer, i.e. first the sample such as e.g. plasma, in particular 90 µl, is incubated, in particular for 180 sec, with the reagent 1, in particular 70 µl, and afterwards the reagent 2, in particular 40 µl, is added and the time to clot is recorded. The particular clotting times measured for dabigatran are shown in Table 9, which is an example of results obtained in spiked NPP samples.

In the case of rivaroxaban or apixaban in a sample, PiCT® Method 4 together with e.g. ACL TOP® 500 analyzer may be used, wherein DRC is generated with extrapolation of the relevant clotting times. The results are shown in Table 10, which is an example of results obtained in spiked NPP samples.

Evaluation if the level of NOACs in a sample are low enough to define this as non-critical situation is a further object of the present invention. To do this determination, the sample may be selected from a fluid, such as in particular from human or animal, preferably blood or plasma, and the clotting times measured via PiCT® Method 4 together with e.g. ACL TOP® 500 analyzer. In the case the non-critical level for rivaroxaban or apixaban have to be measured in the sample, first DRCs have to be developed and the relevant clotting times extrapolated. The results are shown in Table 11, which is an example of results obtained in spiked plasma samples. For dabigatran measurement, PiCT® Method 3 described above might be used, together with e.g. the ACL TOP® 500 analyzer. The results are shown in Table 11 using spiked plasma samples.

The present invention comprises the following embodiments, which are only examples and not intended to limit the scope of the present invention:

1. A method for the determination of the presence of an inhibitor of coagulation in a sample, preferably selected from blood or plasma, using only one coagulation-based test, in particular prothrombinase-induced clotting test (PiCT®).
2. A method according to Embodiment 1 to identify whether or not an anticoagulant is present in a sample, preferably selected from humans or animals, more preferably selected from blood or plasma, using prothrombinase-induced clotting test (PiCT®), wherein the start reagent is added to the sample before the mixing with activator reagent.
3. A method according to Embodiment 1 to determine which kind of new oral anticoagulants (NOACs) is present in a sample, preferably selected from humans or animals, more preferably selected from blood or plasma, using prothrombinase-induced clotting test (PiCT®).
4. A method according to Embodiment 1 to determine which kind of anticoagulant is present in a sample, preferably selected from humans or animals, more preferably selected from blood or plasma, using prothrombinase-induced clotting test (PiCT®) combined with aPTT and/or PT.
5. The method according to Embodiment 4, wherein the sample comprises an anticoagulant selected from the group consisting of UFH, LMWH, hirudin, fondaparinux, argatroban, dabigatran, rivaroxaban and apixaban.
6. A method according to Embodiment 1 for quantification the effect of anticoagulants in a sample, preferably selected from humans or animals, more preferably selected from blood or plasma, using prothrombinase-induced clotting test (PiCT®).
7. A method according to Embodiment 1 for evaluation of the level of NOACs in a sample, more preferably selected from blood or plasma, using prothrombinase-induced clotting test (PiCT®).
8. Use of a combination of prothrombin time (PT), activated partial thromboplastin time (aPTT) and prothrombinase-induced clotting test (PiCT®) for determination of inhibitors of coagulation in a sample, preferably selected from blood or plasma.
9. Use according to Embodiment 8, wherein the inhibitors of coagulation are selected from direct thrombin and factor Xa inhibitors.
10. Use according to any one of Embodiments 8 or 9, wherein within the prothrombinase-induced clotting test the activator can be added before or after the addition of the start reagent.

The following examples are illustrative only and are not intended to limit the scope of the invention in any way.

EXAMPLES

Stock solutions of anticoagulants were prepared in deionized water for UFH (250 IU/mL, WHO standard 07/328, NIBSC), LMWH (250 IU/mL, Fragmin®, Pfizer), and lepirudin (0.5 mg/mL, (Refludan®, Bayer HealthCare Pharmaceuticals Inc) or in DMSO for rivaroxaban (0.5 mg/mL, Alsachim, France) and apixaban (2 mg/mL, Alsachim) or in 0.1M HCl for dabigatran (Alsachim), and were stored at −20° C. Fondaparinux (5 mg/mL, injectable solution, Arixtra®, GlaxoSmithKlines) was stored at 4° C. Anticoagulants were further diluted with deionized water and spiked in NPP prepared from 24 healthy donors (Universitätsklinikum Würzburg, Germany) for PiCT® measurements. The final concentrations of DMSO or HCl in NPP did not exceed 0.15% and 0.4 mM respectively, and did not affect coagulation.

Example 1: PiCT® Adaptations and Determination of Reference Ranges (RR)

As a starting point, the RR for four different types of anticoagulants had to be established as described above. These have to be adapted to the testing system and also to the kind of drug, as e.g. in the case of fondaparinux (PiCT® Method 2) or dabigatran/argatroban (PiCT® Method 3). The results are shown in Table 2 wherein the results are given using fresh plasma from 17 healthy donors.

TABLE 2

Establishing the RR on the ACL TOP ® 500. The clotting time (RR, borderline, out of range) is given in seconds, indicating the mean and the lower and upper ranges (in parentheses).

| Method | RR |
|---|---|
| PiCT ® Method 1 | 27.6 (24.4-30.7) |
| PiCT ® Method 2 | 40.0 (31.9-48.1) |
| PiCT ® Method 3 | 44.7 (38.1-51.3) |
| PiCT ® Method 4 | 29.6 (21.4-37.9) |
| HemosIL ™ aPTT SP | 25.4-36.9 |
| HemosIL ™ PT recombiplastin | 9.4-12.5 |

Protocols and pipetting schemes designed for ACL TOP® 500 are described in Table 3. To assess the potential of Pefakit® PiCT® to evaluate anticoagulant effects of most common anticoagulant drugs, DRCs were performed using NPP spiked with increasing levels of UFH, LMWH, fondaparinux, hirudin, rivaroxaban, apixaban or dabigatran. The details of the different methods, i.e. PiCT® Method 1 to 4, are described in the text.

TABLE 3 pipetting scheme for the 4 different PiCT ® Methods described in the text, wherein "P" means plasma in μl, "A" means activator reagent in μl, "S" means start reagent in μl, and "I" means incubation time in seconds.

| PiCT ® methods | Protocol for ACL TOP ® 500 | Best DRC fit for |
|---|---|---|
| Method 1 | P-50/A-50/I-180/S-50 | UFH, LMWH, hirudin |
| Method 2 | P-75/A-65/I-180/S-35 | Fondaparinux |
| Method 3 | P-90/A-70/I-180/S-40 | Argatroban, dabigatran |
| Method 4 | P-140/S-45/I-160/A-40 | Rivaroxaban, apixaban |

PiCT® Method 4 was identified to offer best results. It consists of inverting the order of reagents' addition to plasma. PiCT® is very sensitive to low levels of NOACs.

Example 2: Pefakit® PiCT® as a Tool to Identify Whether a Plasma Sample Contains an Anticoagulant PiCT® Method 4, which is an inverted PiCT®, was developed as new method to achieve best DRCs for rivaroxaban and apixaban. After calculation of the RR for the different kind of anticoagulants (see Example 1) samples of NPP spiked with incremental amounts of anticoagulants were used in the ACL TOP® 500, wherein 45 μl start reagent was incubated with 140 μl plasma for 60 sec. The time to clot was recorded after addition of 40 μl of activator (i.e. so-called inverted PiCT®). The result is shown in Table 4, wherein the number of samples (NPP) spiked with incremental amounts of anticoagulants (AC) is indicated (n), i.e. indicated as "treatment". Every sample with a result starting from a certain threshold above the RR contains an anticoagulant, which is true for all drugs listed in the Table.

TABLE 4 identification of anticoagulants in plasma samples using PiCT ® Method 4. The baseline means the RR in a sample without the addition of any drug and is shown as mean and as whole range (in brackets). "Conc." means concentration of the anticoagulant per ml of sample. Numbers in bold indicates a clotting time out of range, i.e. presence of a drug in the sample, wherein the negative control, i.e. within RR is underlined.

| Treatment | Conc. | Clotting time with PiCT ® Method 4 [sec] | AC present yes/no |
|---|---|---|---|
| Baseline | 0 | 29.6 (21.4-37.9) n = 6 | no |
| UFH | 0.3 IU | 146 (n = 2) | yes |
| LMWH | 0.4 IU | 129 (n = 2) | |
| hirudin | 0.4 μg | 300 (n = 2) | |
| fondaparinux | 0.3 μg | 57 (n = 2) | |
| argatroban | 0.3 μg | 147 (n = 2) | |
| dabigatran | 20 ng | 60 (n = 3) | |
| | 35 ng | 80 (n = 3) | |
| rivaroxaban | 20 ng | 70 (n = 3) | |
| | 35 ng | 80 (n = 3) | |
| apixaban | 20 ng | 45 (n = 3) | |
| | 35 ng | 54 (n = 3) | |

Using this method, low amounts of all NOACs, UFH, LMWH, hirudin, fondaparinux or argatroban could be detected as shown in Table 4.

Example 3: Pefakit® PiCT® as a Tool to Determine which NOAC is Present in a Sample With the normal PiCT®, i.e. PiCT® Method 1, wherein 50 μl of plasma is mixed with the same amount of reagent 1 (PiCT® activator), incubated for 180 sec and mixed with the same amount of reagent 2 (PiCT® start reagent) in a ACL TOP® 500 analyzer, the presence of NOACs cannot be determined in a sample. This is true even at high levels of said drugs in the sample, i.e. in the range of 300 ng/ml. Thus, in order to determine which NOAC is present in the sample, a combination of PiCT® Method 1 and PiCT® method 4 has to be used (see above for detailed description). To confirm this, spiked plasma samples with different levels of NOACs were prepared and the clotting time measured using first PiCT® Method 1 followed by PiCT® Method 4. The result is shown in Table 5. In the case of rivaroxaban or apixaban present in a tested sample, PiCT® Method 1 is within the range (indicated by the grey background color) whereas PiCT® Method 4 is out of range (indicated in bold). In case of dabigatran present in the sample, both PiCT® Method 1 (which had to be adapted, i.e. PiCT® Method 3) and 4 are out of range as indicated in bold.

TABLE 5 distinction between different NOACs present in a sample determined by a subsequent performance of PiCT ® Method 1 (PiCT ® Method 3 for dabigatran) and PiCT ® Method 4. Results within the RR are indicated by underline, results above the RR are marked in bold. For more details see text or legend to Table 4.

| Treatment | Conc. | Clotting time with PiCT ® Method 1 [sec] | Clotting time with PiCT ® Method 4 [sec] | NOAC present |
|---|---|---|---|---|
| Baseline | 0 | 27.6 (24.4-30.7) n = 17 | 29.6 (21.4-37.9) n = 17 | no |
| rivaroxaban | 20 ng | 17 (n = 3) | 70 (n = 3) | rivaroxaban or apixaban |
|  | 35 ng | 18 (n = 3) | 80 (n = 3) |  |
|  | 300 ng | 29.3 (n = 2) | 162.1 (n = 2) |  |
| apixaban | 20 ng | 18 (n = 3) | 45 (n = 3) |  |
|  | 35 ng | 18 (n = 3) | 54 (n = 3) |  |
|  | 300 ng | 24.9 (n = 2) | 124.3 (n = 2) |  |
| dabigatran | 20 ng | 37 (n = 3) | 60 (n = 3) | dabigatran |
|  | 35 ng | 45 (n = 3) | 80 (n = 3) |  |
|  | 300 ng | 117.5 (n = 2) | 278.1 (n = 2) |  |

Example 4: Pefakit® PiCT® as a Tool to Further Determine the Nature of an and Coagulant in a Plasma Sample In order to address the above question, i.e. to determine the nature of an anticoagulant in a sample, a combination of several methods has to be performed, including PiCT® Method 1, PiCT® Method 4, aPTT (HemosIL™ aPTT SP), PT (HemosIL™ PT recombiplastin), and sometimes even a modified PiCT® Method 1 wherein polybrene has been added. In order to simulate this, plasma samples spiked with different levels of anticoagulants were analyzed using the ACL TOP® 500 analyzer. The results are shown in Table 6. For each drug, a specific pattern was obtained, i.e. clotting times within the RR and clotting times above the RR, depending on the used testing method, which is unique at least for the class of anticoagulant or even for a specific anticoagulant.

TABLE 6 scheme for determination of what kind of anticoagulant is present in spiked plasma samples. Only mean values are given. The "n" refers to the number of healthy donors. For more details see text and legend to Tables 4 or 5.

| Treatment | Concentration | Clotting time with PiCT ® Method 1 [sec] | Clotting time with PiCT ® Method 4 [sec] | Clotting time with aPTT [sec] | Clotting time with PT [sec] | Clotting time with PiCT ® Method 1 + polybrene [sec] |
|---|---|---|---|---|---|---|
| Baseline | 0 | 27.0 n = 6 | 34.4 n = 6 | 28.7 n = 6 | 10.9 n = 6 |  |
| UFH | 0.3 IU | 78.5 n = 2 | 146.0 n = 2 | 66.9 n = 2 | 11.2 n = 2 | 32.0 n = 2 |
|  | 0.8 IU | 119.1 n = 2 | 300 n = 2 | 195.8 n = 2 | 11.4 n = 2 | 32.0 n = 2 |

TABLE 6-continued scheme for determination of what kind of anticoagulant is present in spiked plasma samples. Only mean values are given. The "n" refers to the number of healthy donors. For more details see text and legend to Tables 4 or 5.

| Treatment | Concentration | Clotting time with PiCT® Method 1 [sec] | Clotting time with PiCT® Method 4 [sec] | Clotting time with aPTT [sec] | Clotting time with PT [sec] | Clotting time with PiCT® Method 1 + polybrene [sec] |
|---|---|---|---|---|---|---|
| LMWH | 0.4 IU | 81.2 | 128.9 | 48.0 | 10.9 | 31.1 |
|  |  | n = 2 | n = 2 | n = 2 | n = 2 | n = 2 |
|  | 1.0 IU | 123.3 | 300 | 81.9 | 11.1 | 32.4 |
|  |  | n = 2 | n = 2 | n = 2 | n = 2 | n = 2 |
| Hirudin | 0.4 µg | 88.9 | 300.0 | 60.6 | 11.8 | 89.5 |
|  |  | n = 2 | n = 2 | n = 2 | n = 2 | n = 2 |
|  | 2.5 µg | 264.5 | 300.0 | 108.8 | 14.6 | 258.0 |
|  |  | n = 2 | n = 2 | n = 2 | n = 2 | n = 2 |
| Fondaparinux | 0.3 mg | 53.8 | 56.6 | 33.2 | 11.0 |  |
|  |  | n = 2 | n = 2 | n = 2 | n = 2 |  |
|  | 1.3 mg | 84.7 | 138.9 | 35.1 | 11.4 |  |
|  |  | n = 2 | n = 2 | n = 2 | n = 2 |  |
| Argatroban | 0.3 µg | 98.5 | 147.4 | 61.7 | 15.0 | 85.6 |
|  |  | n = 2 | n = 2 | n = 2 | n = 2 | n = 2 |
|  | 1.5 µg | 150.3 | 300 | 106.2 | 31.2 | 126.4 |
|  |  | n = 2 | n = 2 | n = 2 | n = 2 | n = 2 |
| Dabigatran | 50 ng | 56.2 | 100.7 | 39.6 | 11.4 | 59.7 |
|  |  | n = 5 | n = 5 | n = 4 | n = 4 | n = 2 |
|  | 300 ng | 117.5 | 278.1 | 75.9 | 14.4 | 103.8 |
|  |  | n = 2 | n = 2 | n = 2 | n = 2 | n = 2 |
| Rivaroxaban | 50 ng | 19.0 | 83.6 | 34.5 | 12.2 |  |
|  |  | n = 5 | n = 9 | n = 4 | n = 4 |  |
|  | 200 ng | 25.5 | 132.8 | 49.6 | 20.3 |  |
|  |  | n = 3 | n = 5 | n = 2 | n = 2 |  |
| Apixaban | 50 ng | 18.9 | 54.4 | 31.0 | 11.2 |  |
|  |  | n = 5 | n = 11 | n = 4 | n = 4 |  |
|  | 200 ng | 22.3 | 151.0 | 36.4 | 14.5 |  |
|  |  | n = 2 | n = 8 | n = 2 | n = 2 |  |

In case of a measurement using PiCT® Method 1 and PiCT® Method 4, wherein the clotting time determined with the first method is within the RR but the time measured with the second method is above the RR, the anticoagulant present in the sample is either apixaban or rivaroxaban. Further tests have been performed, i.e. the aPTT or PT in order to distinguish between both anticoagulants: in case of rivaroxaban, with both tests the clotting times were above the RR—but only at higher doses, such as in the range of 200 ng or more (see Table above). If, for example, both the results from PiCT® Method 1 and 4 are above the RR but the aPTT and PT revealed clotting times within the RR, the drug present in the sample is fondaparinux.

Example 5: Pefakit® PiCT® as a Tool to Quantify the Effect of an Anticoagulant

Depending on the drug used, the protocols to determine the quantitative effect of an anticoagulant might differ, i.e., using different testing methods, including the ones listed in Table 1 showing the RRs for the various methods. If the effect of heparins or hirudins, such as e.g. UFH, LMWH and hirudin, is to be quantified, Pefakit® PiCT® with PiCT® Method 1 turned out to be useful, which is shown in Table 7A-C showing DRC in NPP samples spiked with UFH (Table 7A), LMWH (Table 7B) or hirudin (Table 7C) as measured with PiCT® Method 1 and ACL TOP® 500 analyzer. Only mean values are given. For the baseline, i.e. no anticoagulant was present in the sample, the number of measurements was n=6 with a clotting time of 24 seconds measured with PiCT® Method 1.

TABLE 7A

PiCT® Method 1 using NPP spiked with UFH and n = 4.
For more details see text and legend to Table 4.

| Concentration [IU/ml] | 0.1 | 0.2 | 0.3 | 0.5 | 0.7 | 0.9 | 1.1 | 1.3 | 1.5 | 1.6 |
|---|---|---|---|---|---|---|---|---|---|---|
| Clotting time [sec] | 30 | 45 | 62 | 86 | 102 | 113 | 123 | 132 | 143 | 147 |

TABLE 7B

PiCT® Method 1 using NPP spiked with LMWH and n = 4.
For more details see text and legend to Table 4.

| Concentration [IU/ml] | 0.1 | 0.2 | 0.3 | 0.4 | 0.5 | 0.7 | 0.9 | 1.0 | 1.2 | 1.4 |
|---|---|---|---|---|---|---|---|---|---|---|
| Clotting time [sec] | 37 | 47 | 57 | 67 | 76 | 92 | 108 | 114 | 124 | 132 |

TABLE 7C

PiCT ® Method 1 using NPP spiked with hirudin and n = 4.
For more details see text and legend to Table 4.

| Concentration [µg/ml] | 0.2 | 0.4 | 0.6 | 0.9 | 1.3 | 1.7 | 2.0 | 2.4 | 2.8 | 3.0 |
|---|---|---|---|---|---|---|---|---|---|---|
| Clotting time [sec] | 41 | 55 | 69 | 86 | 113 | 142 | 158 | 183 | 209 | 219 |

For fondaparinux, PiCT® Method 2 was determined to be useful. Examples of results obtained with NPP samples on ACL TOP® 500 analyzer are shown in Table 8.

TABLE 8

DRC in NPP samples spiked with fondaparinux as measured with PiCT ® Method 2. Only mean values are given. The number of measurement was n = 4. Clotting time for the baseline, i.e. no anticoagulant present in the sample, was 39 seconds measured with PiCT ® Method 2.

| Concentration [µg/ml] | 0.2 | 0.4 | 0.5 | 0.6 | 0.9 | 1.1 | 1.3 | 1.5 | 1.8 | 2.0 |
|---|---|---|---|---|---|---|---|---|---|---|
| Clotting time [sec] | 78 | 92 | 98 | 103 | 120 | 122 | 133 | 139 | 148 | 155 |

With regards to dabigatran and argatroban, the DRC was established using PiCT® Method 3, the relevant clotting times were extrapolated with the particular conditions as described herein. For all measurements, the ACL TOP® 500 analyzer was used making use of NPP samples spiked with incremental amounts of anticoagulant covering both average peak or trough (see Stangier J, Clin Pharmacokinet 2008, 47:47-59; van Ryn J, Thromb Haemost 2010, 103:1116-1127; Baglin T, J Thromb Haemost. 2013 Jan. 24). Examples of results obtained with NPP samples spiked with either dabigatran (Table 9A) or argatroban (Table 9B) are presented below.

TABLE 9A

DRC in NPP samples spiked with dabigatran as measured with PiCT ® Method 3. Only mean values are given. The number of measurements was n = 4. Clotting time for the baseline, i.e. no anticoagulant present in the sample, was 45 seconds measured with PiCT ® Method 3.

| Concentration [ng/ml] | 5 | 10 | 50 | 100 | 200 | 300 | 400 | 500 | 600 | 750 |
|---|---|---|---|---|---|---|---|---|---|---|
| Clotting time [sec] | 56 | 70 | 122 | 153 | 190 | 207 | 220 | 234 | 245 | 253 |

TABLE 8B

DRC in NPP samples spiked with argatroban as measured with PiCT ® Method 3. Only mean values are given. The number of measurements ("n") was n = 4. Clotting time for the baseline, i.e. no anticoagulant present in the sample, was 45 seconds measured with PiCT ® Method 3.

| Concentration [µg/ml] | 0.2 | 0.4 | 0.6 | 0.8 | 1.0 | 1.2 | 1.4 | 1.6 | 1.8 | 2.0 |
|---|---|---|---|---|---|---|---|---|---|---|
| Clotting time [sec] | 113 | 145 | 162 | 179 | 198 | 204 | 210 | 232 | 234 | 240 |

Regarding rivaroxaban or apixaban, DRC was established making use of PiCT® Method 4 with extrapolation of relevant clotting times associated with the particular conditions. The following are examples of clotting times obtained in ACL TOP® 500 analyzer making use of NPP samples spiked with incremental amounts of anticoagulant levels covering both average peak and trough concentrations of rivaroxaban (see Mueck W, Thromb Haemost 2008, 100: 453-461; Xu X S, Br J Clin Pharmacol 2012, 74:86-97; Baglin T, J Thromb Haemost. 2013 Jan. 24) as shown in Table 10A or apixaban (see Raghavan N, Drug Metab Dispos 2009, 37:74-81; Frost C, Br J Clin Pharmacol 2012, 75:476-487; Frost C, Br J Clin Pharmacol 2013, 76:776-786) as shown in Table 10B. Only mean values are given. For the baseline, i.e. no anticoagulant was present in the sample, the number of measurements was n=4 with a clotting time of 54 seconds measured with PiCT® Method 4.

TABLE 10A

PiCT ® Method 4 using NPP spiked with rivaroxaban and n = 4. For more details see text.

| Concentration [ng/ml] | 5 | 10 | 50 | 100 | 200 | 300 | 400 | 500 | 600 |
|---|---|---|---|---|---|---|---|---|---|
| Clotting time [sec] | 71 | 83 | 118 | 149 | 191 | 220 | 248 | 270 | 278 |

TABLE 10B

PiCT ® Method 4 using NPP spiked with apixaban
and n = 4. For more details see text.

| Concentration [ng/ml] | 5 | 10 | 50 | 100 | 200 | 300 | 400 | 500 | 600 | 750 |
|---|---|---|---|---|---|---|---|---|---|---|
| Clotting time [sec] | 65 | 74 | 109 | 136 | 167 | 197 | 210 | 233 | 259 | 268 |

Example 6: Pefakit® PICT® as a Tool to Evaluate if NOAC Levels are Low Enough

For answering this question with regards to rivaroxaban or apixaban, DRC was generated making use of PiCT® Method 4 (see above). The relevant clotting times associated with the particular conditions were extrapolated. All data were obtained using the ACL TOP® 500 analyzer and plasma samples spiked with anticoagulant levels corresponding to concentration in the plasma reported as wash off levels. The result is shown in Table 11.

TABLE 11 use of PiCT ® Method 4 and plasma samples spiked with different low concentrations of two anticoagulants, i.e. rivaroxaban and apixaban. For more details see text.

|  | PiCT ® method 4 clotting time |
|---|---|
| Rivaroxaban: |  |
| 20 ng/mL | 70 sec (n = 3) |
| 35 ng/mL | 80 sec (n = 3) |
| Apixaban: |  |
| 20 ng/mL | 45 sec (n = 3) |
| 35 ng/mL | 54 sec (n = 3) |

In order to evaluate the level of dabigatran in a sample, DRC was generated making use of PiCT® Method 3, the relevant clotting times associated with the particular conditions were extrapolated. All data were obtained using the ACL TOP® 500 analyzer and plasma samples spiked with anticoagulant levels corresponding to concentration in the plasma reported as wash off levels. The result is shown in Table 12.

TABLE 12 use of PiCT ® Method 3 and plasma samples spiked with different low concentrations of dabigatran. For more details see text.

|  | PiCT ® method 3 clotting time |
|---|---|
| Dabigatran: |  |
| 20 ng/mL | 84 sec (n = 11) |
| 40 ng/mL | 109 sec (n = 11) |

The invention claim is:

1. A method of analyzing a patient sample comprising:
(a) measuring clotting time in the sample via standard prothrombinase-induced clotting time (PiCT) comprising steps in a sequential order: adding to the sample a defined amount of PiCT activator, incubating the sample with the activator at 37° C., adding a start reagent, and measuring time to clot; and
(b) measuring clotting time in the sample via inverted PiCT comprising steps in a subsequent order: adding to the sample the start reagent, incubating the sample with the start reagent at 37° C. for a time period from 60 seconds to 160 seconds, adding a PiCT activator, and measuring time to clot, wherein the patient sample is blood or plasma.

2. The method of claim 1 further comprising:
(c) measuring clotting time in the sample via aPTT; or
(d) measuring clotting time in the sample via PT.

3. The method of claim 1 further comprising:
(c) measuring clotting time in the sample via aPTT; and
(d) measuring clotting time in the sample via PT.

4. The method of claim 1 further comprising:
(e) adding polybrene to the sample and measuring clotting time in the sample via standard prothrombinase-induced clotting time (PiCT) comprising adding to the sample comprising polybrene a defined amount of PiCT activator, incubating the sample with the activator at 37° C., adding the start reagent, and measuring the time to clot; or
(f) adding polybrene to the sample and measuring clotting time in the sample via inverted PiCT comprising adding to the sample comprising polybrene the start reagent, incubating the sample with the start reagent at 37° C., adding a PiCT activator, and measuring the time to clot.

5. The method of claim 3 further comprising:
(e) adding polybrene to the sample and measuring clotting time in the sample via standard prothrombinase-induced clotting time (PiCT) comprising adding to the sample comprising polybrene a defined amount of PiCT activator, incubating the sample with the activator at 37° C., adding the start reagent, and measuring the time to clot; and
(f) adding polybrene to the sample and measuring clotting time in the sample via inverted PiCT comprising adding to the sample comprising polybrene the start reagent, incubating the sample with the start reagent at 37° C., adding a PiCT activator, and measuring the time to clot.

6. The method of claim 1, wherein the patient is bleeding or is at risk of bleeding.

7. The method of claim 1, wherein the patient has ingested an unknown new oral anticoagulant (NOAC) drug.

8. The method of claim 1 used in a point-of-care system.

9. A method of identifying an anticoagulant drug in a patient sample comprising:
(a) measuring clotting time in the sample via standard prothrombinase-induced clotting time (PiCT) comprising steps in a sequential order: adding to the sample a defined amount of PiCT activator, incubating the sample with the activator at 37° C., adding a start reagent, and measuring time to clot; and
(b) measuring clotting time in the sample via inverted PiCT comprising steps in a subsequent order: adding to the sample the start reagent, incubating the sample with the start reagent at 37° C. for a time period from 60 seconds to 160 seconds, adding a PiCT activator, and measuring time to clot, wherein the patient sample is blood or plasma.

10. The method of claim 9 further comprising:
(c) measuring clotting time in the sample via aPTT; or
(d) measuring clotting time in the sample via PT.

11. The method of claim 9 further comprising:
(c) measuring clotting time in the sample via aPTT; and
(d) measuring clotting time in the sample via PT.

12. The method of claim 9 further comprising:
(e) adding polybrene to the sample and measuring clotting time in the sample via standard prothrombinase-induced clotting time (PiCT) comprising adding to the sample comprising polybrene a defined amount of PiCT activator, incubating the sample with the activator at 37° C., adding the start reagent, and measuring the time to clot; or
(f) adding polybrene to the sample and measuring clotting time in the sample via inverted PiCT comprising adding to the sample comprising polybrene the start reagent, incubating the sample with the start reagent at 37° C., adding a PiCT activator, and measuring the time to clot.

13. The method of claim 9 further comprising:
(e) adding polybrene to the sample and measuring clotting time in the sample via standard prothrombinase-induced clotting time (PiCT) comprising adding to the sample comprising polybrene a defined amount of PiCT activator, incubating the sample with the activator at 37° C., adding the start reagent, and measuring the time to clot; and
(f) adding polybrene to the sample and measuring clotting time in the sample via inverted PiCT comprising adding to the sample comprising polybrene the start reagent, incubating the sample with the start reagent at 37° C., adding a PiCT activator, and measuring the time to clot.

14. The method of claim 9, wherein the patient is bleeding or is at risk of bleeding.

15. The method of claim 9, wherein the patient has ingested an unknown new oral anticoagulant (NOAC) drug.

16. The method of claim 9 used in a point-of-care system.

17. The method of claim 9, wherein the patient has ingested an inhibitor of coagulation factor IIa or coagulation factor Xa.

* * * * *